United States Patent
Guevremont et al.

(10) Patent No.: US 6,799,355 B2
(45) Date of Patent: Oct. 5, 2004

(54) APPARATUS AND METHOD FOR TANDEM ICP/FAIMS/MS

(75) Inventors: Roger Guevremont, Gloucester (CA); Randy Purves, Gloucester (CA); David Barnett, Orleans (CA); Gholamreza Javahery, Kettleby (CA); William Ronald Stott, King City (CA)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 10/221,479

(22) PCT Filed: Mar. 14, 2001

(86) PCT No.: PCT/CA01/00313

§ 371 (c)(1),
(2), (4) Date: Sep. 13, 2002

(87) PCT Pub. No.: WO01/69220

PCT Pub. Date: Sep. 20, 2001

(65) Prior Publication Data

US 2003/0213904 A9 Nov. 20, 2003

(51) Int. Cl.[7] .................................................. H01J 49/40
(52) U.S. Cl. .......................................... 25/287; 250/288
(58) Field of Search ................................. 250/278, 288

(56) References Cited

U.S. PATENT DOCUMENTS

| | | | |
|---|---|---|---|
| 4,501,965 A | * | 2/1985 | Douglas ..................... 250/288 |
| 5,106,468 A | | 4/1992 | Chimenti |
| 5,420,424 A | | 5/1995 | Carnahan et al. |
| 5,723,861 A | | 3/1998 | Carnahan et al. |
| 5,736,739 A | | 4/1998 | Uber et al. |
| 5,763,876 A | | 6/1998 | Pertinarides et al. |
| 5,789,745 A | | 8/1998 | Martin et al. |
| 5,801,379 A | | 9/1998 | Kouznetsov |
| 5,847,386 A | * | 12/1998 | Thomson et al. ........... 250/288 |
| 5,869,831 A | | 2/1999 | De La Mora et al. |
| 6,041,734 A | | 3/2000 | Raoux et al. |
| 6,124,592 A | | 9/2000 | Spangler |
| 6,162,709 A | | 12/2000 | Raoux et al. |
| 6,323,482 B1 | | 11/2001 | Clemmer et al. |
| 6,495,823 B1 | | 12/2002 | Miller et al. |
| 6,504,149 B2 | | 1/2003 | Guevremont et al. |
| 6,512,224 B1 | | 1/2003 | Miller et al. |
| 6,621,077 B1 | | 9/2003 | Guevremont et al. |
| 6,639,212 B1 | | 10/2003 | Guevremont et al. |
| 6,653,627 B2 | | 11/2003 | Guevremont et al. |
| 2001/0030285 A1 | | 10/2001 | Miller et al. |
| 2003/0020012 A1 | | 1/2003 | Guevremont et al. |
| 2003/0038235 A1 | | 2/2003 | Guevremont et al. |
| 2003/0057367 A1 | | 3/2003 | Guevremont et al. |
| 2003/0057369 A1 | | 3/2003 | Guevremont et al. |
| 2003/0089847 A1 | | 5/2003 | Guevremont et al. |
| 2003/0150985 A1 | | 8/2003 | Guevremont et al. |

FOREIGN PATENT DOCUMENTS

RU 2105296 2/1998

OTHER PUBLICATIONS

Purves et al. "Electrospray Ionization High–Field Asymmetric Waveforn Ion Mobility Spectrometry–Mass Spectrometry", Analytical Chemistry, vol. 71n No. 13, Jul. 1, 1999.*

(List continued on next page.)

Primary Examiner—John R. Lee
Assistant Examiner—James J. Leybourne
(74) Attorney, Agent, or Firm—Freedman & Associates

(57) ABSTRACT

A method and an apparatus for selectively transmitting ions produced by an inductively coupled plasma ionization technique is disclosed. Ions produced within the plasma source are provided to a FAIMS analyzer within a low pressure chamber of a mass spectrometer and in fluid communication with the plasma source for receiving ions therefrom. The ions are separated in FAIMS and at least some of the ions are provided to the mass spectrometer after separation.

9 Claims, 4 Drawing Sheets

OTHER PUBLICATIONS

U.S. patent application Ser. No. 09/762,238, Guevremont et al., Not published.

Carr et al., "Plasma Chromatography", (1984), Plenum Press, New York.

Mason et al., "Transport Properties of Ions in Gases", (1988), Wiley, New York.

Buryakov et al., "A New Method of Separation of Multi-Atomic Ions by Mobility at Atmospheric Pressure using a High–Frequency Amplitude–Asymmetric Strong Electric Field", Int. J. Mass Spectrom. Ion Processes, No. 128, pp. 143–148, (1993), Elsevier Science Publishers B.V.

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96–009, pp. 87–95, (1996), Framingham, MA, USA.

Riegner et al., "Qualitative Evaluation of Field Ion Spectrometry for Chemical Warfare Agent Detection", Proceedings of the 45th ASMS Conference on Mass Spectrometry and Allied Topics, Palm Springs, California, pp. 473, (1997).

Purves et al., "Mass Spectrometric Characterization of a High–Field Asymmetric Waveform Ion Mobility Spectrometer", Review of Scientific Instruments, vol. 69, No. 12, pp. 4094–4105, (Dec. 1998), American Institute of Physics.

Guevremont et al., "Atmospheric Pressure Ion Focusing in a High–Field Asymmetric Waveform Ion Mobility Spectrometer", Review of Scientific Instruments, vol. 70, No. 2, pp. 1370–1\383, (Feb. 1999), American Institute of Physics.

Krylov, "A Method of Reducing Diffusion Losses in a Drift Spectrometer", Tech Phys., vol. 44, No. 1, pp. 113–116, (1999), American Institute of Physics.

* cited by examiner

APPARATUS AND METHOD FOR TANDEM ICP/FAIMS/MS

This application claims the benefit of provisional application 60/189,085 filed on Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1t_2+V_2t_1=0$; for example +2000 V for 10 $\mu$s followed by −1000 V for 20 $\mu$s. The peak voltage during the shorter, high voltage portion of the waveform is called the "dispersion voltage" or DV in this disclosure.

During the high voltage portion of the waveform, the electric field causes the ion to move with a transverse y-axis velocity component $v_1=K_hE_{high}$, where $E_{high}$ is the applied field, and $K_h$ is the high field ion mobility under ambient electric field, pressure and temperature conditions. The distance traveled is $d_1=v_1t_2=K_hE_{high}t_2$, where $t_2$ is the time period of the applied high voltage. During the longer duration, opposite polarity, low voltage portion of the asymmetric waveform, the y-axis velocity component of the ion is $v_2=KE_{low}$, where K is the low field ion mobility under ambient pressure and temperature conditions. The distance traveled is $d_2=v_2t_1=KE_{low}t_1$. Since the asymmetric waveform ensures that $(V_1t_2)+(V_2t_1)=0$, the field-time products $E_{high}t_2$ and $E_{low}t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h>K$, the ion experiences a net displacement from its original position relative to the y-axis. For example, positive ions of type A travel farther during the positive portion of the waveform, for instance $d_1>d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to K is similarly different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV. is obtained. It is a significant limitation of early FAIMS devices which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30, 1995, B. L. Carnahan and A. S. Tarassove disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focusing of ions by the use of asymmetric waveforms has been discussed above. For completeness, the behavior of those ions that are not focused within the analyzer region of a cylindrical geometry FAIMS is described here, briefly. As discussed previously, those ions having high field ion mobility properties that are other than suitable for focusing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focused, for example at DV 2500 volts, CV–11 volts in a given geometry, it would seem reasonable to expect that the ion is also focused if the polarity of DV and CV are reversed, for instance DV of –2500 volts and CV of +11 volts. This, however, is not observed and in fact the reversal of polarity in this manner creates a mirror image effect of the ion-focusing behavior of FAIMS. The result of such polarity reversal is that the ions are not focused, but rather are extremely rapidly rejected from the device,. The mirror image of a focusing valley, is a hill-shaped potential surface. The ions slide to the center of the bottom of a focusing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focusing behavior described above, except that the ion-focusing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focusing. If the CV and DV are suitable for the focusing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as disclosed in a copending PCT application in the name of R. Guevremont and R. Purves, the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a prat thereof; electrodes that are spheres or a part thereof: electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately-collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated under a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focusing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

The analysis of certain samples, for instance inorganic compounds containing metal atoms, requires an ionization source based upon a plasma torch to produce the ions for analysis. Unfortunately, a prior art inductively couple plasma (ICP) source also produces an abundance of ions resulting from ionization of the bath gas molecules or atoms. The plasma is not a selective ionization source, and significant background ion intensity relative to the trace ions of interest is typically produced. Further unfortunately, the plasma in some cases produces interfering ions having a same mass-to-charge ratio (m/z) as the ions of interest. For example, ions of the structure argon oxide (ArO+) with m/z 56 are produced in an argon plasma, and are isobaric with the analyte ion of iron (Fe+) also with m/z 56.

It would be advantageous to provide a method and a system for reducing the intensity of the background ions produced within a plasma source that are transmitted to a mass analyzer with the ions of interest. It would be further advantageous to provide a method and a system to separate ions of interest from interfering ions having a same m/z ratio that are formed in the plasma source.

OBJECT OF THE INVENTION

In order to overcome these and other limitations of the prior art, it is an object of the present invention to provide an apparatus for separating ions produced by an ICP and having a substantially same mass-to-charge ratio prior to providing the ions to a mass analyzer for detection.

SUMMARY OF THE INVENTION

In accordance with the invention there is provided an analyzer comprising: an inductively coupled plasma/mass spectrometer comprising a plasma ionization source for producing ions and a mass analyzer within a low pressure region, characterized in that between the plasma ionization source and the mass analyzer is disposed a FAIMS analyzer.

In accordance with the invention there is provided a method for separating ions comprising the steps of:
producing ions within an inductively coupled plasma ionization source;
providing an asymmetric waveform to an electrode for forming an electric field within the FAIMS analyzer region to support selective transmission of ions within the FAIMS analyzer region;

transporting the ions through the electric field to perform a separation thereof; and, providing the ions after separation to a mass spectrometer for analysis.

DETAILED DESCRIPTION OF THE INVENTION

Figure 1:
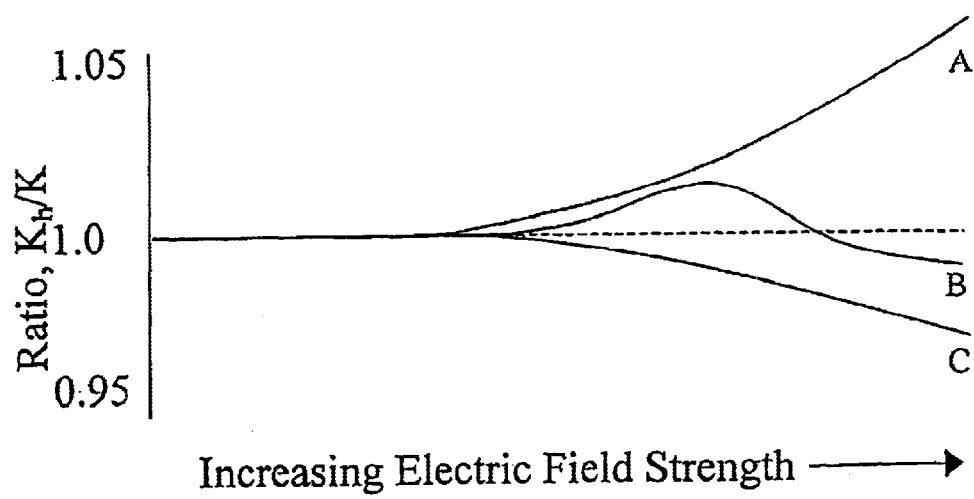
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is other than separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
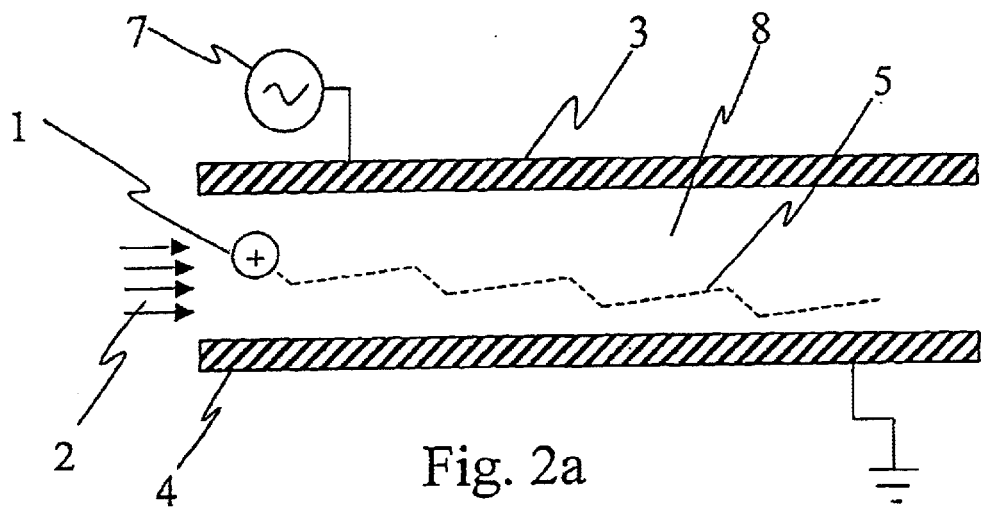
FIG. 2a illustrates the trajectory of an ion between two parallel plate electrodes under the influence of the electrical potential V(t)
Figure 2B:
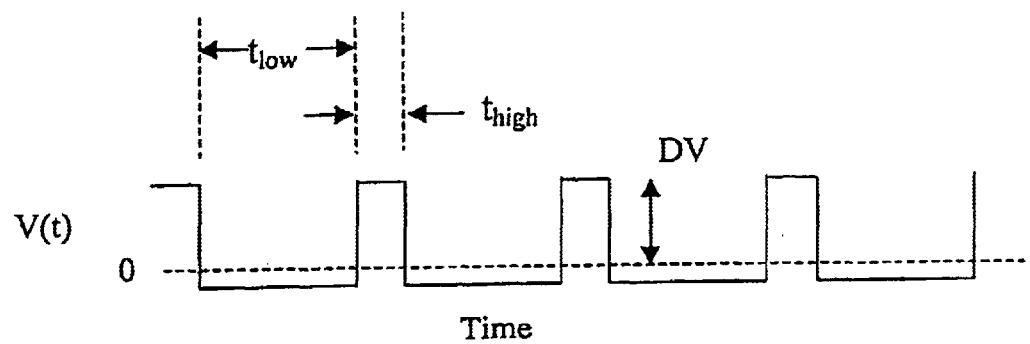
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential while the other plate 3 has an asymmetric waveform described by V(t), applied to it. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 8 between the first and second spaced apart electrode plates, 3 and 4, respectively, the ion 1 experiences a net displacement from its original position relative to the plates 3 and 4 as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figure 3:
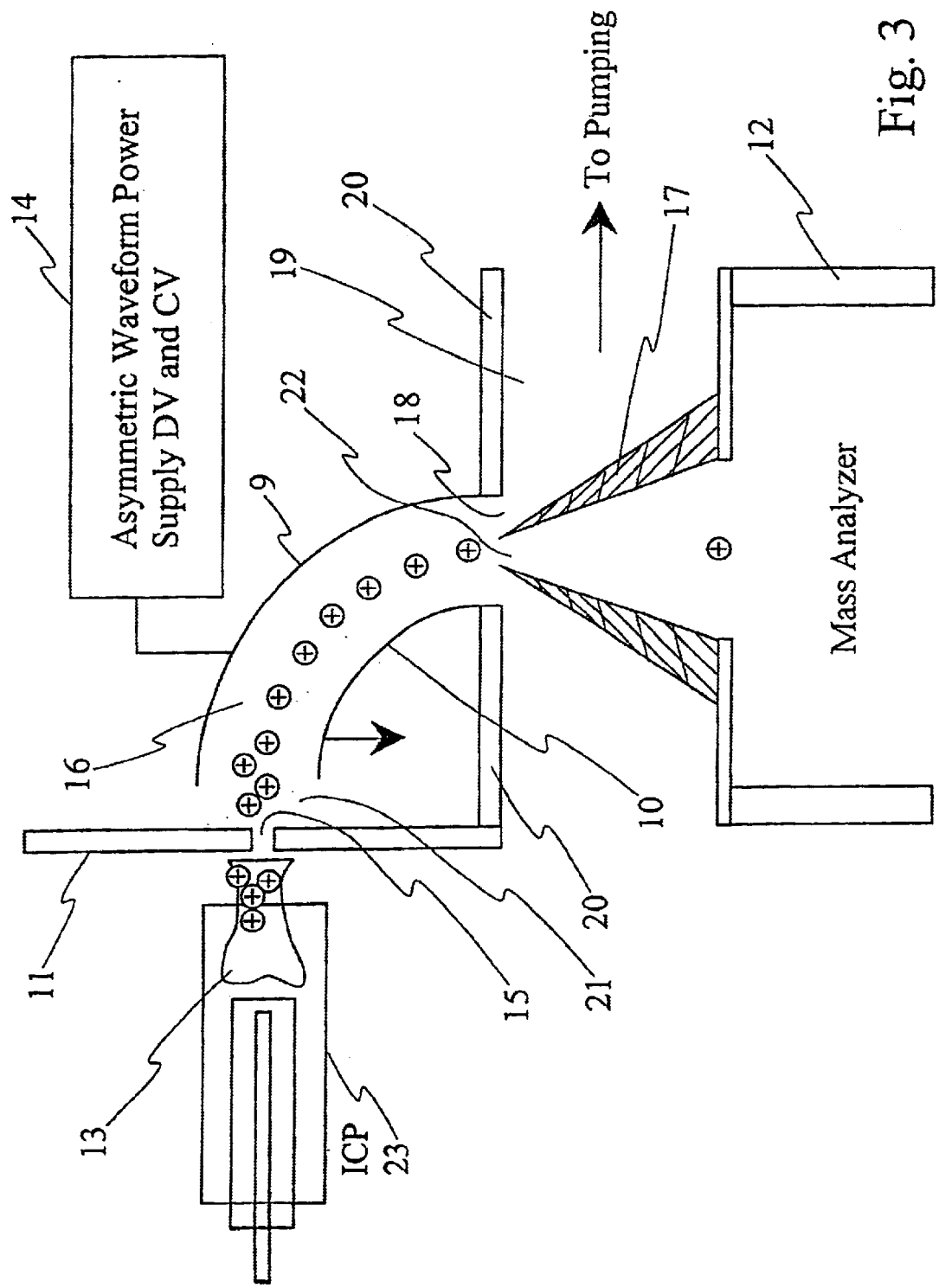
FIG. 3 shows a simplified block diagram of an ICP/FAIMS/MS system according to a first embodiment of the invention.

Referring to FIG. 3, a simplified block diagram of an ICP/FAIMS/MS system according to a first embodiment of the invention is shown. Two electrodes 9 and 10, defining a FAIMS analyzer region 16 therebetween, are disposed on the low pressure side of an orifice plate 11, for example within a differentially pumped region of an interface leading into a mass analyzer shown generally at 12. The ions are produced by an inductively couple plasma 13 which is supported in a special torch assembly 23 in a known manner. For the sake of clarity and brevity, the gas flow system, and the electrical and electronic components, for example power supplies, that are necessary to establish the plasma are not shown in FIG. 3.

Still referring to FIG. 3, an asymmetric waveform and a low voltage dc compensation voltage is applied to electrode 9 by a power supply 14. In this embodiment FAIMS is operating at a gas pressure lower than standard atmospheric pressure, such that the voltage necessary to effect a change in ion mobility characteristic of high electric field is reduced compared to the voltage required at approximately atmospheric pressure. For instance, the effect of electric field strength on ion mobility is considered in terms of E/N, where E is the electric field strength and N is the number density of the bath gas. For example, if a DV of 3000 volts is necessary to achieve a desired effect at atmospheric pressure, the same effect is obtained at DV of 300 volts when the gas pressure is reduced to 0.1 of an atmosphere. This relationship between field strength and gas number density well known for FAIMS apparatus with electrode geometries based upon one of two parallel plates and two concentric substantially overlapping cylinders. At higher E/N the frequency of the waveform may be increased in order to limit the distances of the ion trajectory during each cycle of the waveform, thus minimizing ion loss through collisions with the electrodes.

Still referring to FIG. 3, the applied DV is lower than the DV that is needed to operate FAIMS at substantially atmospheric pressure. The two FAIMS electrodes 9 and 10 are curved electrodes in spaced apart stacked arrangement, such that an approximately uniform spacing is maintained between the electrodes 9 and 10 along the FAIMS analyzer region 16. Advantageously, the curvature along the electrode bodies 9 and 10 results in the formation of electric fields within analyzer region 16 that are non-uniform in space by the application of the voltages by power supply 14. This non-uniform in space electric field is optionally produced by making the FAIMS electrodes substantially cylindrical or spherical in shape, however, many other shapes and combinations of shapes are used to achieve the same effect.

The ions that pass through an orifice 15 in the orifice plate 11 are carried to the FAIMS analyzer region 16 between electrodes 9 and 10 by a flow of a carrier gas originating from the gas passing into the low pressure region through the orifice 15. Those ions having the appropriate high field-strength mobility properties for transmission under the conditions of DV and CV are focused in the analyzer region 16 and selectively transmitted to a skimmer cone 17. The ions are transported through the analyzer region 16 by the carrier gas which flows toward a gap 18 between the FAIMS analyzer region 16 and the skimmer cone 17. The skimmer cone 17 is within a chamber 19 of an interface leading into the mass spectrometer 12, the chamber 19 is evacuated to low gas pressure in the vicinity of the gap 18 by a mechanical pump (not shown) connected to the chamber 19. A gas barrier 20 serves to ensure that the gas pressure in the vicinity of the gap 18 is slightly lower than the pressure near the region 21 immediately behind orifice 15. Since the pressure in region 21 is higher than the pressure in the gap 18, the carrier gas flows along the FAIMS analyzer region in a direction generally towards the gap 18. Of course, other means for transporting the ions through the FAIMS analyzer region 16 are optionally provided, for instance an electric field.

Still referring to FIG. 3, the ions that are selectively transmitted through the FAIMS analyzer region 16 are transferred to the mass spectrometer through the orifice 22 in skimmer cone 17. The ions are directed toward the orifice 22 of skimmer cone 17 by an electric field formed between FAIMS and the skimmer cone 17, the electric field produced by the application of dc voltages to the FAIMS and to the skimmer cone 17.

Of course, the hot argon plasma of a conventional ICP is not compatible with FAIMS, and the FAIMS is located within the first low pressure-chamber of the mass spectrometer as previously described with reference to the first embodiment of the present invention shown in FIG. 3. Optionally, additional provisions for thermally isolating the FAIMS analyzer from the ICP source are provided. Further optionally, a cooling system is provided to maintain the vicinity of the FAIMS analyzer at approximately ambient laboratory temperature.

Figure 4:
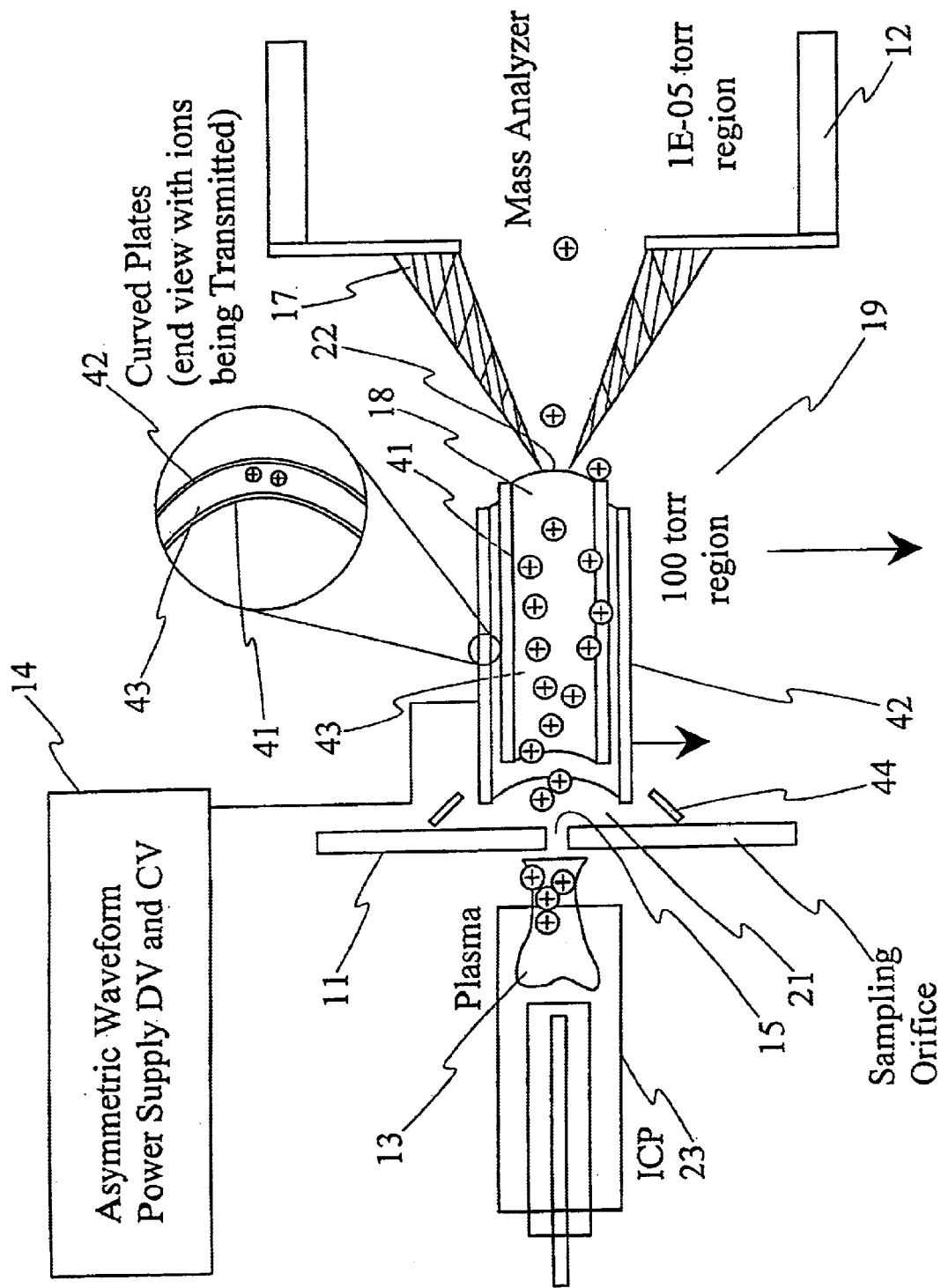
FIG. 4 shows a simplified block diagram of an ICP/FAIMS/MS system according to a second embodiment of the invention.

Referring to FIG. 4, a simplified block diagram of an ICP/FAIMS/MS system according to a second embodiment of the invention is shown. Two FAIMS electrodes 41 and 42 defining a FAIMS analyzer region 43 therebetween, are disposed on the low pressure side of an orifice plate 11, for example within a differentially pumped region of an interface leading into a mass analyzer shown generally at 12. The ions are produced by an inductively couple plasma 13 which is supported in a special torch assembly 23 in a known manner. For the sake of clarity and brevity, the gas flow system, and the electrical and electronic components, for example power supplies, that are necessary to establish the plasma are not shown in FIG. 3.

Still referring to FIG. 4, an asymmetric waveform and a low voltage dc compensation voltage is applied to electrode 42 by a power supply 14. In this embodiment FAIMS is operating at a gas pressure lower than standard atmospheric pressure, such that the voltage necessary to effect a change in ion mobility characteristic of high electric field is reduced compared to the voltage required at approximately atmospheric pressure. For instance, the effect of electric field strength on ion mobility is considered in terms of E/N, where E is the electric field strength and N is the number density of the bath gas. For example, if a DV of 3000 volts is necessary to achieve a desired effect at atmospheric pressure, the same effect is obtained at DV of 300 volts when the gas pressure is reduced to 0.1 of an atmosphere. This relationship between field strength and gas number density well known for FAIMS apparatus with electrode geometries based upon one of two parallel plates and two concentric substantially overlapping cylinders. At higher E/N the frequency of the waveform may be increased in order to limit the distances of the ion trajectory during each cycle of the waveform, thus minimizing ion loss through collisions with the electrodes.

Referring still to FIG. 4, the electrodes 41 and 42 are provided as curved plates in a spaced apart stacked arrangement such that such that an approximately uniform spacing is maintained between the electrodes 41 and 42 along the FAIMS analyzer region 43. Advantageously, the curvature across the electrode bodies 41 and 42 results in the formation of electric fields within analyzer region 43 that are non-uniform in space by the application of the voltages by power supply 14. This non-uniform in space electric field is optionally produced by making the FAIMS electrodes substantially cylindrical or spherical in shape, however, many other shapes and combinations of shapes are used to achieve the same effect. The curvature of the plates is shown most clearly in an inset view at the top of FIG. 4. In this inset view, the ions travel into and out of the plane of the drawing.

Still referring to FIG. 4, the ions that pass through an orifice 15 in the orifice plate 11 are carried to the FAIMS analyzer region 43 between electrodes 41 and 42 by a flow of a carrier gas originating from the gas passing into the low pressure region through the orifice 15. Those ions having the appropriate high field-strength mobility properties for transmission under the conditions of DV and CV are focused in the analyzer region 16 and selectively transmitted to a skimmer cone 17. The ions are transported through the analyzer region 43 by the carrier gas, which flows toward a gap 18 between the FAIMS analyzer region 43 and the skimmer cone 17. The skimmer cone 17 is within a chamber 19 of an interface leading into the mass spectrometer 12, the chamber 19 is evacuated to low gas pressure in the vicinity of the gap 18 by a mechanical pump (not shown) connected to the chamber 19. A gas barrier 44 serves to ensure that the gas pressure in the vicinity of the gap 18 is slightly lower than the pressure near the region 21 immediately behind orifice 15. Since the pressure in region 21 is higher than the pressure in the gap 18, the carrier gas flows along the FAIMS analyzer region in a direction generally towards the gap 18. Of course, other means for transporting the ions through the FAIMS analyzer region 43 are optionally provided, for instance an electric field.

Still referring to FIG. 4, the ions that are selectively transmitted through the FAIMS analyzer region 43 are transferred to the mass spectrometer 12 through the orifice 22 in skimmer cone 17. The ions are directed toward the orifice 22 of skimmer cone 17 by an electric field formed between FAIMS and the skimmer cone 17, the electric field produced by the application of dc voltages to the FAIMS and to the skimmer cone 17.

Of course, FAIMS electrodes 41 and 42 are optionally provided with a shape other than curved plates, for instance as flat parallel plate electrodes. However, in order to efficiently extract the selectively transmitted ions from a FAIMS analyzer region defined by the space between flat plate electrodes, a third approximately equally spaced flat plate electrode is additionally required, as disclosed in a co-pending PCT application in the name of R. Guevremont and R. Purves, the contents of which are herein incorporated by reference.

Of course, the hot argon gas (plasma) of a conventional ICP is not compatible with FAIMS, and the FAIMS is located within the first low pressure-chamber of the mass spectrometer as previously described with reference to the second embodiment of the present invention shown in FIG. 4. Optionally, additional provisions for thermally isolating the FAIMS analyzer from the ICP source are provided. Further optionally, a cooling system is provided to maintain the vicinity of the FAIMS analyzer at approximately ambient laboratory temperature.

Figure 5:
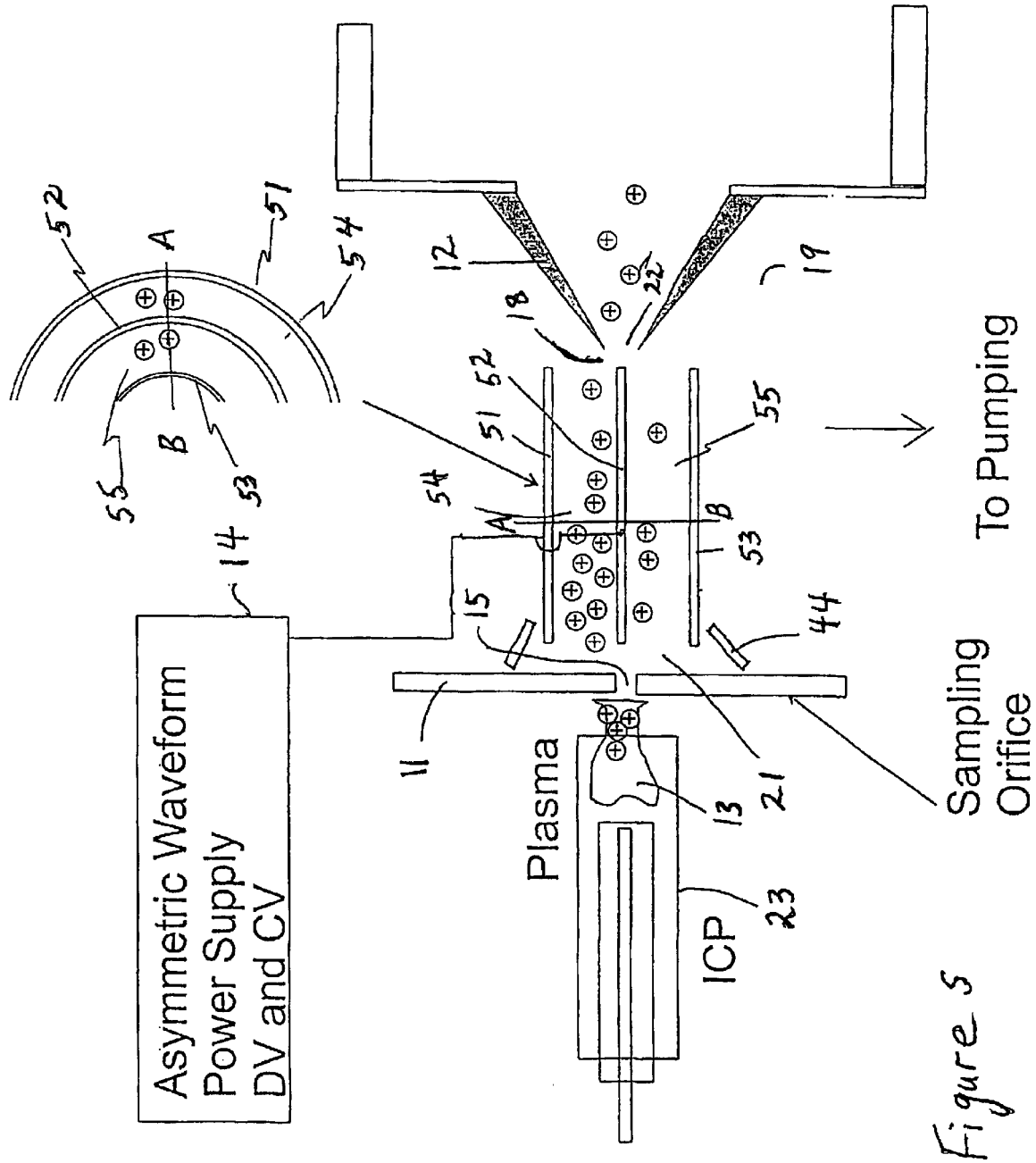
FIG. 5 shows a simplified block diagram of an ICP/FAIMS/MS system according to a third embodiment of the invention; and, FIG. 5a shows a cross sectional view taken along the line A–B in FIG. 5.

Referring to FIG. 5, a simplified block diagram of an ICP/FAIMS/MS system according to a third embodiment of the invention is shown. Three FAIMS electrodes 51 and 52 defining a FAIMS analyzer region 54 therebetween, are disposed on th low pressure side of an orifice plate 11, for example within a differentially pumped region fan interface leading into a mass analyzer shown generally at 12. The ions are produced b an inductively couple plasma 13 which is supported in a special torch assembly 3 in a known manner. For the sake of clarity and brevity, the gas flow system, and the electrical and electronic components, for example power supplies, that are necessary to establish the plasma are not shown in FIG. 5.

Still referring to FIG. 5, an asymmetric waveform and a low voltage dc compensation voltage is applied to FAIMS middle electrode 52 by a power supply 14. In this embodiment FAIMS is operating at a gas pressure lower than standard atmospheric pressure, such that the voltage necessary to effect a change in ion mobility characteristic of high electric field is reduced compared to the voltage required at approximately atmospheric pressure. For instance, the effect of electric field strength on ion mobility is considered in terms of E/N, where E is the electric field strength and N is the number density of the bath gas. For example, if a DV of 3000 volts is necessary to achieve a desired effect at atmospheric pressure, the same effect is obtained at DV of 300 volts when the gas pressure is reduced to 0.1 of an atmosphere. This relationship between field strength and gas number density well known for FAIMS apparatus with electrode geometries based upon one of two parallel plates and two concentric substantially overlapping cylinders. At higher E/N the frequency of the waveform may be increased in order to limit the distances of the ion trajectory during each cycle of the waveform, thus minimizing ion loss through collisions with the electrodes.

Referring still to FIG. 5, the electrodes 51, 52 and 53 are provided curved plates in a spaced apart stacked arrangement such that such that an approximately uniform spacing is maintained between the electrodes 51 and 52 along the FAIMS analyzer region 54, and a substantially same uniform spacing is maintained between the electrodes 52 and 53 along the FAIMS analyzer region 55. Advantageously, the curvature across the electrode bodies 51, 52 and 53 results in the formation of electric fields within analyzer region 54 and 55 that are non-uniform in space, by the application of the voltages by power supply 14. This non-uniform in space electric field is optionally produced by making the FAIMS electrodes substantially cylindrical or spherical in shape, however, many other shapes and combinations of shapes are used to achieve the same effect. The curvature of the plates is shown most clearly at FIG. 5a. which is a cross sectional view taken alone the line A–B In FIG. 5a, the ions travel into and out of the plane of the drawing.

Of course, the non-constant in space electric field established within analyzer region 54 between the FAIMS electrodes 51 and 52 is a different non-constant in space electric field compared to the electric field that is established within analyzer region 55 between the FAIMS electrodes 51 and 52. A first species of ions having first mobility properties as a function of electric field strength are selectively transmitted within analyzer region 54, and a second different species of ions having second different mobility properties as a function of electric field strength are selectively transmitted within analyzer region 55 in parallel with the first species of ion.

Still referring to FIG. 5, the ions that pass through an orifice 15 in the orifice plate 11 are carried to one of the FAIMS analyzer regions 54 and 55 between electrodes 51 and 52, and between electrodes 52 and 53, respectively, by a flow of a carrier gas originating from the gas passing into the low pressure region through the orifice 15. Those ions having the appropriate high field-strength mobility properties for transmission under the conditions of DV and CV are focused within one of the FAIMS analyzer regions, for instance FAIMS analyzer region 54, and selectively transmitted to a skimmer cone 17. Of course, other species of ions will be focused within the FAIMS analyzer region 55. The ions are transported through the analyzer region 54 by the carrier gas which flows toward a gap 18 between the FAIMS analyzer region 54 and the skimmer cone 17. The skimmer cone 17 is within a chamber 19 of an interface leading into the mass spectrometer 12, the chamber 19 is evacuated to low gas pressure in the vicinity of the gap 18 by a mechanical pump (not shown) connected to the chamber 19. A gas barrier 44 serves to ensure that the gas pressure in the vicinity of the gap 18 is slightly lower than the pressure near the region 21 immediately behind orifice 15. Since the pressure in region 21 is higher than the pressure in the gap 18, the carrier gas flows along the FAIMS analyzer region in a direction generally towards the gap 18. Optionally, the leading and trailing edges of at least curved electrode plate 52 are provided with curved edges for focusing the ions and for diverting the ions away from the electrode 52 such that the ions other than collide therewith, thereby improving ion transmission efficiency. Of course, other means for transporting the ions through the FAIMS analyzer regions 54 and 55 are optionally provided, for instance an electric field.

Still referring to FIG. 5, the ions that are selectively transmitted through the FAIMS analyzer region 54 are transferred to the mass spectrometer 12 through the orifice 22 in skimmer cone 17. The ions are directed toward the orifice 22 of skimmer cone 17 by an electric field formed between FAIMS and the skimmer cone 17, the electric field produced by the application of dc voltages to the FAIMS and to the skimmer cone 17.

Of course, the hot argon plasma of a conventional ICP is not compatible with FAIMS, and the FAIMS is located within the first low pressure-chamber of the mass spectrometer as previously described with reference to the third embodiment of the present invention shown in FIG. 5. Optionally, additional provisions for thermally isolating the FAIMS analyzer from the ICP source are provided. Further optionally, a cooling system is provided to maintain the vicinity of the FAIMS analyzer at approximately ambient laboratory temperature.

It will be obvious to one of skill in the art that separating different ionic species having identical mass-to-charge ratios is other than possible using a prior art mass spectrometer absent FAIMS. Further, it will be obvious to one of skill in the art that separating different ionic species having similar mass-to-charge ratios, for instance mass-to-charge ratios that differ only by several hundredths of an atomic mass unit (amu), requires a high resolution mass spectrometer. It is a disadvantage of high resolution mass spectrometers that the initial capital cost of purchase is high, and it is a further disadvantage that the ongoing operating costs of providing an expert operator and expensive pumping apparatus are also high. Additionally, a high resolution mass spectrometer suffers from lower sensitivity compared to low resolution mass spectrometers, such that a system including a high resolution mass spectrometer as part of a detection systems suffers from an overall lower ion transmission efficiency and a resultant decreased sensitivity.

It is an advantage of the present invention as described with reference to the first, second and third embodiments that FAIMS optionally separates ions produced by the ICP source which have equal m/z. FAIMS separates ions in dependence upon a difference in ion mobility properties as a function of electric field strength, and therefore effects the separation of ionic species that are other than separated in the mass spectrometer 12. For instance an appropriate combination of DV and CV is applied to at least an electrode of FAIMS to selectively transmit an analyte ion through the FAIMS analyzer region to pass through an orifice leading to a low resolution mass spectrometer. Those ions that are other than of interest and which have mobility properties that are other than suitable for being selectively transmitted through the FAIMS analyzer region, for instance the background ions, are caused to collide with a part of FAIMS and are rejected from the device. Since the number of analyte ions arriving at the mass spectrometer relative to the number of background ions is increased, the detector response relative to the level of the noise is also increased, such that the sensitivity of the instrument is increased. Optionally, the geometry of the FAIMS electrodes is selected to maximize ion transmission efficiency through FAIMS, such that the sensitivity of an ICP/FAIMS/MS instrument is improved further.

It is a further advantage of FAIMS that the capability of FAIMS to separate ions having similar high field mobility properties improves as the m/z ratio of the ion is decreased. This is consistent with the requirements of the system described herein, where FAIMS is required to separate ions of typically low m/z values, for instance argon oxide (ArO+) with m/z 56 and the ion of iron (Fe+) also with m/z 56. The typically low mass-to-charge values of the ions of interest is also consistent with the operation of a very inexpensive, low resolution mass spectrometer. Advantageously, in addition to improving sensitivity for the detection of analyte ions and removing isobaric ions interfering with the analysis the analyte ions, the ICP/FAIMS/MS system of the present invention is compact, inexpensive and simpler to operate compared to a prior art ICP/high-resolution mass spectrometer.

Further advantageously, FAIMS separates the ions of interest from the abundance of background ions that are other than of interest formed in the plasma.

Of course, numerous other embodiments could be envisioned, without departing significantly from the teachings of the present invention.

What is claimed is:

1. An analyzer comprising:
   an inductively coupled plasma/mass spectrometer comprising a plasma ionization source for producing ions and a mass analyzer within a low pressure region, characterized in that between the plasma ionization source and the mass analyzer is disposed a FAIMS analyzer,
   the FAIMS analyzer comprising two spaced apart electrodes defining a FAIMS analyzer reunion therebetween and having a first ion inlet for introducing ions into the FAIMS analyzer region and a first ion outlet for extracting ions from the FAIMS analyzer region; and,
   an orifice plate having a second ion outlet for providing ions from the plasma ionization source to the first ion inlet,
   wherein the FAIMS analyzer is disposed on a low pressure side of the orifice plate.

2. An apparatus according to claim 1 wherein the two spaced apart electrodes are curved electrodes.

3. An apparatus according to claim 1 wherein the FAIMS analyzer comprises a gas inlet for providing a flow of at least a gas through the analyzer region between the two spaced apart electrodes for transporting the ions through the analyzer region in a direction generally towards the first ion outlet.

4. An apparatus according to claim 1 wherein the FAIMS comprises a first gas inlet for providing a flow of at least a gas through the analyzer region for, in use, directing at least some of the ions generally towards the first ion outlet.

5. An apparatus according to claim 1 comprising an electrode for providing an electric field for selectively transporting the ions generally towards the first ion outlet.

6. An apparatus according to claim 1 comprising a voltage source for providing a signal to the electrode for providing an electric field for selectively transporting the ions generally towards the first ion outlet.

7. A method for separating ions comprising the steps of:
   producing ions within an inductively coupled plasma ionization source;
   providing an electrode of a FAIMS analyzer within a low pressure region;
   providing an asymmetric waveform and a direct current compensation voltage to the electrode for forming an electric field within the FAIMS analyzer region to support selective transmission of ions within the FAIMS analyzer region;
   transporting the produced ions through the electric field to perform a separation thereof; and,
   providing the ions after separation to a mass spectrometer for analysis.

8. A method according to claim 7 wherein the step of transporting includes the step of providing a flow of at least a gas through the analyzer region.

9. A method according to claim 7 wherein the step of transporting includes the step of providing an electric field for selectively transporting the ions in a direction generally towards the mass spectrometer.

* * * * *

UNITED STATES PATENT AND TRADEMARK OFFICE
CERTIFICATE OF CORRECTION

PATENT NO. : 6,799,355 B2  Page 1 of 1
DATED : October 5, 2004
INVENTOR(S) : Guevremont et al.

It is certified that error appears in the above-identified patent and that said Letters Patent is hereby corrected as shown below:

Title page,
Insert Item -- [60] Related U.S. Application Data
  Provisional Application No. 60/189,085, filed on March 14, 2000. --

Drawings,
Sheet 4, Figure 5, should be replaced with Figure 5 and Figure 5A as shown below:

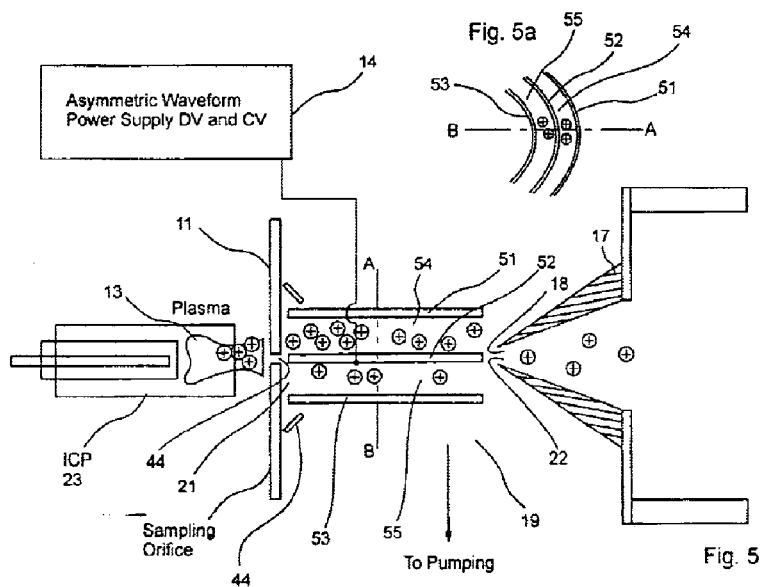

Column 14,
Line 2, for the claim referenced numeral "1", the word "reunion" should read -- region --.

Signed and Sealed this

Twenty-first Day of December, 2004

JON W. DUDAS
*Director of the United States Patent and Trademark Office*